United States Patent [19]
Smith

[11] Patent Number: 5,393,730
[45] Date of Patent: Feb. 28, 1995

[54] NICOTINIC ACID HYDRAZONE COMPOUNDS WHICH HAVE USEFUL HERBICIDAL COMPOSITIONS

[75] Inventor: Philip H. G. Smith, Essex, England

[73] Assignee: Rhone-Poulenc Agriculture Ltd., Essex, England

[21] Appl. No.: 180,309

[22] Filed: Jan. 12, 1994

[30] Foreign Application Priority Data

Jan. 12, 1993 [GB] United Kingdom ............... 9300480

[51] Int. Cl.$^6$ ............... C07D 213/80; A01N 43/40
[52] U.S. Cl. ............... 504/130; 546/262; 546/263; 546/315; 546/316; 546/318
[58] Field of Search ............... 546/316, 318, 262, 263, 546/315; 504/130

[56] References Cited

FOREIGN PATENT DOCUMENTS

| | | |
|---|---|---|
| 0219451 | 4/1987 | European Pat. Off. ............ 504/130 |
| 0222254 | 5/1987 | European Pat. Off. ............ 546/316 |
| 0258182 | 3/1988 | European Pat. Off. ............ 504/130 |
| 0429372 | 5/1991 | European Pat. Off. ............ 546/316 |
| 0555957 | 8/1993 | European Pat. Off. ............ 546/316 |

OTHER PUBLICATIONS

March, Advanced Organic Chemistry, p. 804, 1985.
Chemical Abstracts, vol. 54, No. 17, Abstract 18,509a, Sep. 10, 1960.
Chemical Abstracts, vol. 56, No. 10, Abstract 11561e, May 14, 1962.
Anzini et al., *J. Heterocyclic Chem.*, 29, 1111–1115 (1992).
French et al., *J. Medicinal Chemistry*, vol. 17, No. 2, 172–181 (1974).

*Primary Examiner*—C. Warren Ivy
*Assistant Examiner*—Zinna N. Davis
*Attorney, Agent, or Firm*—Burns, Doane, Swecker & Mathis

[57] ABSTRACT

The invention relates to nicotinic acid hydrazone derivatives of formula I:

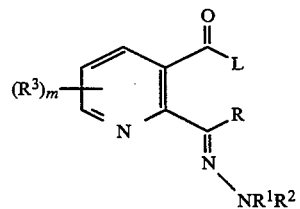

in which the various symbols are as defined in the description, and their use as herbicides or as intermediates in the synthesis of herbicides.

17 Claims, No Drawings

NICOTINIC ACID HYDRAZONE COMPOUNDS WHICH HAVE USEFUL HERBICIDAL COMPOSITIONS

This invention relates to novel nicotinic acid hydrazone derivatives, compositions containing them, processes for their preparation and their use as herbicides or intermediates thereto.

The present invention provides nicotinic acid hydrazone derivatives of formula I:

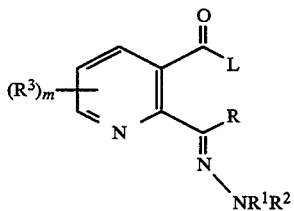

wherein R represents:
the hydrogen atom;
a straight- or branched- chain alkyl, alkenyl or alkynyl group containing up to six carbon atoms optionally substituted by one or more halogen atoms;
a group Het;
a group $—[CR^{41}R^{42}]_n\text{-Het1}$; or
a group $—[CR^{41}R^{42}]_n\text{-(phenyl)-}(R^{31})_p$;
$R^1$ represents:
the hydrogen atom;
a straight- or branched- chain alkyl, alkenyl or alkynyl group containing up to six carbon atoms optionally substituted by one or more halogen atoms;
a group Het; or
a group $—[CR^{41}R^{42}]_n\text{-Het1}$; or
a group $—[CR^{41}R^{42}]_n\text{-(phenyl)-}(R^{32})_q$;
$R^2$ represents:
the hydrogen atom;
a straight- or branched- chain alkyl, alkenyl or alkynyl group containing up to six carbon atoms optionally substituted by one or more halogen atoms; or
phenyl optionally substituted by from one to five groups $R^{31}$ which may be the same or different;
$R^3$ represents:
a halogen atom;
a straight- or branched- chain alkyl, alkenyl or alkynyl group containing up to six carbon atoms optionally substituted by one or more halogen atoms;
—CN; $—CO_2R^4$; $—S(O)_rR^4$; $—NO_2$; $—NR^{41}R^{42}$; —OH; $—COR^4$; $—S(O)_rR^5$; $—CO_2R^5$; $—OR^5$; $—CONR^{41}R^{42}$, $—OSO_2R^5$, $—OSO_2R^6$, $—OCH_2R^5$, $—N(R^{41})COR^6$, $—N(R^{41})SO_2R^5$, $—N(R^{41})SO_2R^6$, $—SO_2NR^{41}R^{42}$, $—Si(R^6)_3$;
phenyl optionally substituted by from one to five groups $R^{31}$; or
a straight- or branched- chain alkoxy group containing up to six carbon atoms optionally substituted by one or more halogen atoms;
L represents:
a hydroxy group;
a straight- or branched- chain alkoxy group containing up to six carbon atoms; or
an amino group $—NR^7R^8$;
$R^{31}$ and $R^{32}$, which may be the same or different, each represents:

a halogen atom;
a straight- or branched- chain alkoxy group containing up to six carbon atoms optionally substituted by one or more halogen atoms;
a straight- or branched- chain alkyl, alkenyl or alkynyl group containing up to six carbon atoms optionally substituted by one or more halogen atoms;
—OH; $—S(O)_rR^4$; $—CO_2R^4$; $—COR^4$; —CN; $—NO_2$; $—NR^{41}R^{42}$; $—S(O)_rR^5$; $—CO_2R^5$; $—OR^5$; $—CONR^{41}R^{42}$, $—OSO_2R^5$, $—OSO_2R^6$, $—OCH_2R^5$, $—N(R^{41})COR^6$, $—N(R^{41})SO_2R^5$, $—N(R^{41})SO_2R^6$, $—SO_2NR^{41}R^{42}$ or $—Si(R^6)_3$;
$R^4$ represents a hydrogen atom or a straight- or branched- chain alkyl group containing up to six carbon atoms optionally substituted by one or more halogen atoms;
$R^{41}$ and $R^{42}$, which may be the same or different, each represents a hydrogen atom or a straight- or branched- chain alkyl group containing up to four carbon atoms optionally substituted by one or more halogen atoms;
$R^5$ represents phenyl optionally substituted by from one to five groups which may be the same or different selected from halogen, nitro, cyano, $R^4$ and $—OR^4$;
$R^6$ represents a straight- or branched- chain alkyl group containing up to six carbon atoms optionally substituted by one or more halogen atoms;
$R^7$ and $R^8$, which may be the same or different, each represents:
the hydrogen atom;
a straight- or branched- chain alkyl group containing up to four carbon atoms optionally substituted by one or more halogen atoms;
phenyl optionally substituted by from one to five groups which may be the same or different selected from halogen, nitro, cyano, $R^4$ and $—OR^4$;
Het represents a 5 or 6 membered heterocycle containing from 3 to 5 carbon atoms in the ring and one or more heteroatoms in the ring selected from nitrogen, oxygen and sulphur, e.g. pyridyl, pyrimidinyl, thienyl, piperidyl or pyrazolyl; optionally substituted by one or more groups $R^{31}$ which may be the same or different;
Het1 represents phenyl or a 5 or 6 membered heterocycle containing from 3 to 5 carbon atoms in the ring and one or more heteroatoms in the ring selected from nitrogen, oxygen and sulphur, optionally substituted by one or more groups $R^{31}$ and wherein two substituents on adjacent positions of the ring, together with the two atoms to which they are attached, form a 5- to 7- membered alicyclic ring (which is optionally unsaturated) or an aromatic ting, optionally containing one or more heteroatoms (preferably selected from oxygen, sulphur and nitrogen, it being understood that a sulphur atom, where present, may be in the form of a group —SO— or $—SO_2—$), wherein the alicyclic or aromatic ring is optionally substituted by one or more groups $R^{51}$ which may be the same or different;
$R^{51}$ is as hereinbefore defined for $R^{31}$ or represents =O or =S;
m represents zero or an integer from one to three; where m is greater than one the groups $R^3$ may be the same or different;
n represents zero, one or two; where n is two, the groups $—(CR^{41}R^{42})—$ may be the same or different;
p represents zero or an integer from one to five; where p is greater than one the groups $R^{31}$ may be the same or different;

q represents zero or an integer from one to five; where q is greater than one the groups $R^{32}$ may be the same or different;

r represents zero, one or two;

and agriculturally acceptable salts thereof.

The nicotinic acid hydrazones of formula I may exist in syn- or anti- isomer forms. Furthermore, in certain cases, the substituents R, $R^1$, $R^2$, $R^3$, $R^{31}$, $R^{32}$, $R^4$, $R^{41}$, $R^{42}$, $R^5$, $R^6$, $R^7$, $R^8$ and $R^{51}$ contribute to optical and/or stereoisomerism. All such forms are embraced by the present invention.

By the term "agriculturally acceptable salts" is meant salts the cations or anions of which are known and accepted in the art for the formation of salts for agricultural or horticultural use. Preferably the salts are water soluble. Suitable salts formed by compounds of formula I which are acidic, e.g. compounds containing a carboxy group, with bases include alkali metal (e.g. sodium and potassium) salts, alkaline earth metal (e.g. calcium and magnesium) salts and ammonium (e.g. diethanolamine, triethanolamine, octylamine, dioctylamine and morpholine) salts.

Suitable acid addition salts, for example formed with the ring nitrogen of the pyridyl nicotinate group of compounds of formula I or with compounds of formula I containing an amino group, include salts with inorganic acids, for example hydrochlorides, sulphates, phosphates and nitrates and salts with organic acids, for example acetic acid. It is to be understood that where reference is made in the specification to the compounds of formula I, such reference is intended to include salts where the context so permits.

Compounds of formula I are useful either as herbicides as described hereinbelow, or as intermediates in the synthesis of herbicidally active compounds, for example as described in the co-pending European Patent Application Number 93300164.4, filed on 12 Jan. 1993 (published as EP 0555957 on Aug. 18, 1993), and British Patent Application No. 9314412.9, filed on 13 Jul. 1993, both incorporated by reference herein in relevant part.

Where the group Het1 represents optionally substituted phenyl or pyridyl with two substituents on adjacent positions of the ring forming a 5- to 7- membered alicyclic ring (which is optionally unsaturated) or an aromatic ring, which contains one or more heteroatoms in the ring, generally there will be from one to three heteroatoms. Examples of the group Het 1 include optionally substituted benzothiazole, benzoxazole, methylenedioxybenzene, benzimidazole, indole and indazole.

Furthermore, where Het1 represents pyridyl optionally substituted by one or two groups $R^{31}$, the two substituents on adjacent atoms of the pyridyl ring which form a 5- to 7- membered alicyclic or aromatic ring may be attached to two carbon atoms or to a carbon and nitrogen atom of the pyridyl ring.

In a preferred embodiment the invention provides compounds of formula (I) above wherein:

R represents:
the hydrogen atom;
a straight- or branched- chain alkyl, alkenyl or alkynyl group containing up to six carbon atoms optionally substituted by one or more halogen atoms;
a group Het;
a group —$[CR^{41}R^{42}]_n$-(phenyl)-$(R^{31})_p$;
$R^1$ represents:
the hydrogen atom;
a straight- or branched- chain alkyl, alkenyl or alkynyl group containing up to six carbon atoms optionally substituted by one or more halogen atoms;
a group Het; or
a group —$[CR^{41}R^{42}]_n$-(phenyl)-$(R^{32})_q$;
$R^2$ represents:
the hydrogen atom;
a straight- or branched- chain alkyl, alkenyl or alkynyl group containing up to six carbon atoms optionally substituted by one or more halogen atoms; or
phenyl optionally substituted by from one to five groups $R^{31}$ which may be the same or different;
$R^3$ represents:
a halogen atom;
a straight- or branched- chain alkyl, alkenyl or alkynyl group containing up to six carbon atoms optionally substituted by one or more halogen atoms; —CN; —$CO_2R^4$; —$S(O)_rR^4$; —$NO_2$; —$NR^{41}R^{42}$; —OH; —$COR^4$; —$S(O)_rR^5$; —$CO_2R^5$; —$OR^5$; —$CONR^{41}R^{42}$, —$OSO_2R^5$, —$OSO_2R^6$, —$OCH_2R^5$, —$N(R^{41})COR^6$, —$N(R^{41})SO_2R^5$, —$N(R^{41})SO_2R^6$, —$SO_2NR^{41}R^{42}$;
phenyl optionally substituted by from one to five groups $R^{31}$; or
a straight- or branched- chain alkoxy group containing up to six carbon atoms optionally substituted by one or more halogen atoms;
L represents:
a hydroxy group;
a straight- or branched- chain alkoxy group containing up to six carbon atoms; or
an amino group —$NR^7R^8$;
$R^{31}$ and $R^{32}$, which may be the same or different, each represents:
a halogen atom;
a straight- or branched- chain alkoxy group containing up to six carbon atoms optionally substituted by one or more halogen atoms;
a straight- or branched- chain alkyl, alkenyl or alkynyl group containing up to six carbon atoms optionally substituted by one or more halogen atoms; —OH; —$S(O)_rR^4$; —$CO_2R^4$; —$COR^4$; —CN; —$NO_2$; —$NR^{41}R^{42}$; —$S(O)_rR^5$; —$CO_2R^5$; —$OR^5$; —$CONR^{41}R^{42}$, —$OSO_2R^5$, —$OSO_2R^6$, —$OCH_2R^5$, —$N(R^{41})COR^6$, —$N(R^{41})SO_2R^5$, —$N(R^{41})SO_2R^6$ or —$SO_2NR^{41}R^{42}$;
$R^4$ represents a hydrogen atom or a straight- or branched-chain alkyl group containing up to six carbon atoms optionally substituted by one or more halogen atoms;
$R^{41}$ and $R^{42}$, which may be the same or different, each represents a hydrogen atom or a straight- or branched-chain alkyl group containing up to four carbon atoms optionally substituted by one or more halogen atoms;
$R^5$ represents phenyl optionally substituted by from one to five groups which may be the same or different selected from halogen, nitro, cyano, $R^4$ and —$OR^4$;
$R^6$ represents a straight- or branched- chain alkyl group containing up to six carbon atoms optionally substituted by one or more halogen atoms;
$R^7$ and $R^8$, which may be the same or different, each represents:
the hydrogen atom;
a straight- or branched- chain alkyl group containing up to four carbon atoms optionally substituted by one or more halogen atoms;

phenyl optionally substituted by from one to five groups which may be the same or different selected from halogen, nitro, cyano, $R^4$ and $-OR^4$;

Het represents a 5 or 6 membered heterocycle containing from 3 to 5 carbon atoms in the ring and one or more heteroatoms in the ring selected from nitrogen, oxygen and sulphur, e.g. pyridyl, pyrimidinyl, thienyl, piperidyl or pyrazolyl; optionally substituted by one or more groups $R^{31}$ which may be the same or different;

m represents zero or an integer from one to three; where m is greater than one the groups $R^3$ may be the same or different;

n represents zero, one or two; where n is two, the groups $-(CR^{41}R^{42})-$ may be the same or different;

p represents zero or an integer from one to five; where p is greater than one the groups $R^{31}$ may be the same or different;

q represents zero or an integer from one to five; where q is greater than one the groups $R^{32}$ may be the same or different; and r represents zero, one or two.

Compounds of formula I wherein n represents zero are preferred.

Further preferred compounds of formula I are those in which L represents $-NR^7R^8$ or, most preferably, hydroxy.

Compounds of formula I in which $R^2$ represents hydrogen are also preferred.

Further preferred compounds of formula I are those wherein R represents phenyl substituted in the 3-position by a group $R^{31}$, preferably a group selected from cyano, $-OCF_3$ and $-CF_3$.

Compounds of formula I in which R represents a group $-(-CR^{41}R^{42})_n$-Het1, wherein Het1 represents phenyl optionally substituted by from one to three groups $R^{31}$ and wherein two substituents in the 2- and 3-positions of the ring, together with the two atoms to which they are attached, form a 5- or 6- membered alicyclic ring (which is optionally unsaturated) or an aromatic ring, containing one or two heteroatoms selected from oxygen, sulphur and nitrogen (e.g. benzothiazole, benzoxazole, methylenedioxybenzene, benzimidazole, indole or indazole), wherein the alicyclic or aromatic ring is optionally substituted by one or more groups $R^{51}$ which may be the same or different; are preferred.

Preferably R represents $-(CR^{41}R^{42})_n$-Het1, wherein n is zero and Het1 represents phenyl substituted in the 2- and 3- positions by a difluoromethylenedioxy group $-OCF_2O-$.

A further preferred class of compounds of formula I are those wherein $R^1$ represents phenyl substituted in the 4-position by a group $R^{32}$, preferably a group selected from chlorine, fluorine and $-CF_3$.

Preferably m represents zero. Where m represents one, compounds of formula I in which $R^3$ represents a group in the 5-position of the pyridyl ring are preferred, especially compounds in which $R^3$ is selected from the group consisting of methyl, chlorine and fluorine.

Particularly important compounds include the following:

1. 2-(3-trifluoromethylbenzoyl)nicotinic acid (4-trifluoromethylphenyl)hydrazone;
2. 2-(3-trifluoromethylbenzoyl)nicotinic acid (2,6-dichloro-4-trifluoromethylphenyl)hydrazone;
3. 2-(3-trifluoromethoxybenzoyl)nicotinic acid (4-trifluoromethylphenyl)hydrazone;
4. 2-(3-trifluoromethylbenzoyl)nicotinic acid (4-fluorophenyl)hydrazone;
5. 2-(3-trifluoromethylbenzoyl)nicotinic acid (N-methyl-N-phenyl)hydrazone;
6. 5-methyl-2-(3-trifluoromethoxybenzoyl)nicotinic acid (4-trifluoromethylphenyl)hydrazone;
7. 2-(2,3-difluoromethylenedioxybenzoyl)nicotinic acid (4-fluorophenyl)hydrazone;
8. N,N-dimethyl-2-(3-trifluoromethylbenzoyl)-nicotinamide (4-trifluoromethylphenyl)hydrazone.

The numbers 1 to 8 are assigned to these compounds for reference and identification hereinafter.

In addition, the compounds of formula (Ia) below in the following Table form part of the present invention:

| $(R^3)_m$ | R | $(R^{32})_q$ | $(R^3)_m$ | R | $(R^{32})_q$ |
|---|---|---|---|---|---|
| — | 3-CN phenyl | 4-Cl | — | 3-CN phenyl | 4-F |
| — | 3-CF3 phenyl | 4-Cl | — | 3-CF3 phenyl | 4-F |
| — | 3-OCF3 phenyl | 4-Cl | — | 3-OCF3 phenyl | 4-F |
| — | 3-SCF3 phenyl | 4-Cl | — | 3-SCF3 phenyl | 4-F |
| — | 2,3-OCF2O-phenyl | 4-Cl | — | 2,3-OCF2O-phenyl | 4-F |
| — | 2-OCF3 phenyl | 4-Cl | — | 2-OCF3 phenyl | 4-F |
| — | 3-OSO2CH3 phenyl | 4-Cl | — | 3-OSO2CH3 phenyl | 4-F |
| — | 3-OCF2H phenyl | 4-Cl | — | 3-OCF2H phenyl | 4-F |
| — | 4-F-3-CF3 phenyl | 4-Cl | — | 4-F-3-CF3 phenyl | 4-F |
| — | 3-CN phenyl | 4-CF3 | — | 3-CN phenyl | 3,4-F2 |
| — | 3-CF3 phenyl | 4-CF3 | — | 3-CF3 phenyl | 3,4-F2 |
| — | 3-OCF3 phenyl | 4-CF3 | — | 3-OCF3 phenyl | 3,4-F2 |
| — | 3-SCF3 phenyl | 4-CF3 | — | 3-SCF3 phenyl | 3,4-F2 |
| — | 2,3-OCF2O-phenyl | 4-CF3 | — | 2,3-OCF2O-phenyl | 3,4-F2 |
| — | 2-OCF3 phenyl | 4-CF3 | — | 2-OCF3 phenyl | 3,4-F2 |
| — | 3-OSO2CH3 phenyl | 4-CF3 | — | 3-OSO2CH3 phenyl | 3,4-F2 |
| — | 3-OCF2H phenyl | 4-CF3 | — | 3-OCF2H phenyl | 3,4-F2 |
| — | 4-F-3-CF3 phenyl | 4-CF3 | — | 4-F-3-CF3 phenyl | 3,4-F2 |
| — | 3-CN phenyl | 3-CF3-4-F | — | 3-CN phenyl | 4-CN |
| — | 3-CF3 phenyl | 3-CF3-4-F | — | 3-CF3 phenyl | 4-CN |
| — | 3-OCF3 phenyl | 3-CF3-4-F | — | 3-OCF3 phenyl | 4-CN |
| — | 3-SCF3 phenyl | 3-CF3-4-F | — | 3-SCF3 phenyl | 4-CN |

-continued

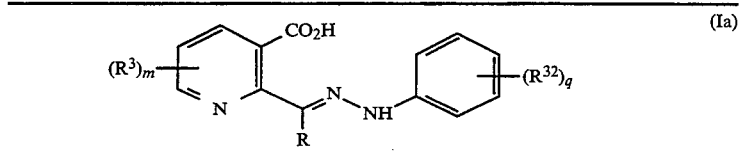

(Ia)

| $(R^3)_m$ | R | $(R^{32})_q$ | $(R^3)_m$ | R | $(R^{32})_q$ |
|---|---|---|---|---|---|
| — | 2,3-OCF2O-phenyl | 3-CF3-4-F | — | 2,3-OCF2O-phenyl | 4-CN |
| — | 2-OCF3 phenyl | 3-CF3-4-F | — | 2-OCF3 phenyl | 4-CN |
| — | 3-OSO2CH3 phenyl | 3-CF3-4-F | — | 3-OSO2CH3 phenyl | 4-CN |
| — | 3-OCF2H phenyl | 3-CF3-4-F | — | 3-OCF2H phenyl | 4-CN |
| — | 4-F-3-CF3 phenyl | 3-CF3-4-F | — | 4-F-3-CF3 phenyl | 4-CN |
| — | 3-CN phenyl | 3-F-4-CN | 5-Cl | 3-CN phenyl | 4-F |
| — | 3-CF3 phenyl | 3-F-4-CN | 5-Cl | 3-CF3 phenyl | 4-F |
| — | 3-OCF3 phenyl | 3-F-4-CN | 5-Cl | 3-OCF3 phenyl | 4-F |
| — | 3-SCF3 phenyl | 3-F-4-CN | 5-Cl | 3-SCF3 phenyl | 4-F |
| — | 2,3-OCF2O-phenyl | 3-F-4-CN | 5-Cl | 2,3-OCF2O-phenyl | 4-F |
| — | 2-OCF3 phenyl | 3-F-4-CN | 5-Cl | 2-OCF3 phenyl | 4-F |
| — | 3-OSO2CH3 phenyl | 3-F-4-CN | 5-Cl | 3-OSO2CH3 phenyl | 4-F |
| — | 3-OCF2H phenyl | 3-F-4-CN | 5-Cl | 3-OCF2H phenyl | 4-F |
| — | 4-F-3-CF3 phenyl | 3-F-4-CN | 5-Cl | 4-F-3-CF3 phenyl | 4-F |
| 5-Cl | 3-CN phenyl | 4-CF3 | 5-Cl | 3-CN phenyl | 3,4-F2 |
| 5-Cl | 3-CF3 phenyl | 4-CF3 | 5-Cl | 3-CF3 phenyl | 3,4-F2 |
| 5-Cl | 3-OCF3 phenyl | 4-CF3 | 5-Cl | 3-OCF3 phenyl | 3,4-F2 |
| 5-Cl | 3-SCF3 phenyl | 4-CF3 | 5-Cl | 3-SCF3 phenyl | 3,4-F2 |
| 5-Cl | 2,3-OCF2O-phenyl | 4-CF3 | 5-Cl | 2,3-OCF2O-phenyl | 3,4-F2 |
| 5-Cl | 2-OCF3 phenyl | 4-CF3 | 5-Cl | 2-OCF3 phenyl | 3,4-F2 |
| 5-Cl | 3-OSO2CH3 phenyl | 4-CF3 | 5-Cl | 3-OSO2CH3 phenyl | 3,4-F2 |
| 5-Cl | 3-OCF2H phenyl | 4-CF3 | 5-Cl | 3-OCF2H phenyl | 3,4-F2 |
| 5-Cl | 4-F-3-CF3 phenyl | 4-CF3 | 5-Cl | 4-F-3-CF3 phenyl | 3,4-F2 |
| 5-Cl | 3-CN phenyl | 3-CF3-4-F | 5-Cl | 3-CN phenyl | 4-CN |
| 5-Cl | 3-CF3 phenyl | 3-CF3-4-F | 5-Cl | 3-CF3 phenyl | 4-CN |
| 5-Cl | 3-OCF3 phenyl | 3-CF3-4-F | 5-Cl | 3-OCF3 phenyl | 4-CN |
| 5-Cl | 3-SCF3 phenyl | 3-CF3-4-F | 5-Cl | 3-SCF3 phenyl | 4-CN |
| 5-Cl | 2,3-OCF2O-phenyl | 3-CF3-4-F | 5-Cl | 2,3-OCF2O-phenyl | 4-CN |
| 5-Cl | 2-OCF3 phenyl | 3-CF3-4-F | 5-Cl | 2-OCF3 phenyl | 4-CN |
| 5-Cl | 3-OSO2CH3 | 3-CF3-4-F | 5-Cl | 3-OSO2CH3 phenyl | 4-CN |
| 5-Cl | 3-OCF2H phenyl | 3-CF3-4-F | 5-Cl | 3-OCF2H phenyl | 4-CN |
| 5-Cl | 4-F-3-CF3 phenyl | 3-CF3-4-F | 5-Cl | 4-F-3-CF3 phenyl | 4-CN |
| 5-F | 3-CN phenyl | 4-CF3 | 5-F | 3-CN phenyl | 3,4-F2 |
| 5-F | 3-CF3 phenyl | 4-CF3 | 5-F | 3-CF3 phenyl | 3,4-F2 |
| 5-F | 3-OCF3 phenyl | 4-CF3 | 5-F | 3-OCF3 phenyl | 3,4-F2 |
| 5-F | 3-SCF3 phenyl | 4-CF3 | 5-F | 3-SCF3 phenyl | 3,4-F2 |
| 5-F | 2,3-OCF2O-phenyl | 4-CF3 | 5-F | 2,3-OCF2O-phenyl | 3,4-F2 |
| 5-F | 2-OCF3 phenyl | 4-CF3 | 5-F | 2-OCF3 phenyl | 3,4-F2 |
| 5-F | 3-OSO2CH3 phenyl | 4-CF3 | 5-F | 3-OSO2CH3 phenyl | 3,4-F2 |
| 5-F | 3-OCF2H phenyl | 4-CF3 | 5-F | 3-OCF2H phenyl | 3,4-F2 |
| 5-F | 4-F-3-CF3 phenyl | 4-CF3 | 5-F | 4-F-3-CF3 phenyl | 3,4-F2 |
| 5-F | 3-CN phenyl | 3-CF3-4-F | 5-F | 3-CN phenyl | 4-CN |
| 5-F | 3-CF3 phenyl | 3-CF3-4-F | 5-F | 3-CF3 phenyl | 4-CN |
| 5-F | 3-OCF3 phenyl | 3-CF3-4-F | 5-F | 3-OCF3 phenyl | 4-CN |
| 5-F | 3-SCF3 phenyl | 3-CF3-4-F | 5-F | 3-SCF3 phenyl | 4-CN |
| 5-F | 2,3-OCF2O-phenyl | 3-CF3-4-F | 5-F | 2,3-OCF2O-phenyl | 4-CN |
| 5-F | 2-OCF3 phenyl | 3-CF3-4-F | 5-F | 2-OCF3 phenyl | 4-CN |
| 5-F | 3-OSO2CH3 phenyl | 3-CF3-4-F | 5-F | 3-OSO2CH3 phenyl | 4-CN |
| 5-F | 3-OCF2H phenyl | 3-CF3-4-F | 5-F | 3-OCF2H phenyl | 4-CN |
| 5-F | 4-F-3-CF3 phenyl | 3-CF3-4-F | 5-F | 4-F-3-CF3 phenyl | 4-CN |
| 5-F | 3-CN phenyl | 4-F | 5-F | 2-OCF3 phenyl | 4-F |
| 5-F | 3-CF3 phenyl | 4-F | 5-F | 3-OSO2CH3 phenyl | 4-F |
| 5-F | 3-OCF3 phenyl | 4-F | 5-F | 3-OCF2H phenyl | 4-F |
| 5-F | 3-SCF3 phenyl | 4-F | 5-F | 4-F-3-CF3 phenyl | 4-F |
| 5-F | 2,3-OCF2O-phenyl | 4-F | 5-CH3 | 2,3-OCF2O-phenyl | 4-F |
| 5-CH3 | 3-CN phenyl | 4-CF3 | 5-CH3 | 3-CN phenyl | 3,4-F2 |
| 5-CH3 | 3-CF3 phenyl | 4-CF3 | 5-CH3 | 3-CF3 phenyl | 3,4-F2 |
| 5-CH3 | 3-OCF3 phenyl | 4-CF3 | 5-CH3 | 3-OCF3 phenyl | 3,4-F2 |
| 5-CH3 | 3-SCF3 phenyl | 4-CF3 | 5-CH3 | 3-SCF3 phenyl | 3,4-F2 |
| 5-CH3 | 2,3-OCF2O-phenyl | 4-CF3 | 5-CH3 | 2,3-OCF2O-phenyl | 3,4-F2 |
| 5-CH3 | 2-OCF3 phenyl | 4-CF3 | 5-CH3 | 2-OCF3 phenyl | 3,4-F2 |
| 5-CH3 | 3-OSO2CH3 phenyl | 4-CF3 | 5-CH3 | 3-OSO2CH3 phenyl | 3,4-F2 |
| 5-CH3 | 3-OCF2H phenyl | 4-CF3 | 5-CH3 | 3-OCF2H phenyl | 3,4-F2 |
| 5-CH3 | 4-F-3-CF3 phenyl | 4-CF3 | 5-CH3 | 4-F-3-CF3 phenyl | 3,4-F2 |
| 5-CH3 | 3-CN phenyl | 3-CF3-4-F | 5-CH3 | 3-CN phenyl | 4-CN |
| 5-CH3 | 3-CF3 phenyl | 3-CF3-4-F | 5-CH3 | 3-CF3 phenyl | 4-CN |
| 5-CH3 | 3-OCF3 phenyl | 3-CF3-4-F | 5-CH3 | 3-OCF3 phenyl | 4-CN |
| 5-CH3 | 3-SCF3 phenyl | 3-CF3-4-F | 5-CH3 | 3-SCF3 phenyl | 4-CN |
| 5-CH3 | 2,3-OCF2O-phenyl | 3-CF3-4-F | 5-CH3 | 2,3-OCF2O-phenyl | 4-CN |
| 5-CH3 | 2-OCF3 phenyl | 3-CF3-4-F | 5-CH3 | 2-OCF3 phenyl | 4-CN |
| 5-CH3 | 3-OSO2CH3 phenyl | 3-CF3-4-F | 5-CH3 | 3-OSO2CH3 phenyl | 4-CN |
| 5-CH3 | 3-OCF2H phenyl | 3-CF3-4-F | 5-CH3 | 3-OCF2H phenyl | 4-CN |
| 5-CH3 | 4-F-3-CF3 phenyl | 3-CF3-4-F | 5-CH3 | 4-F-3-CF3 phenyl | 4-CN |

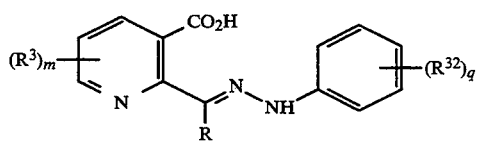

(Ia)

| $(R^3)_m$ | R | $(R^{32})_q$ | $(R^3)_m$ | R | $(R^{32})_q$ |
|---|---|---|---|---|---|
| 5-CH3 | 3-CN phenyl | 4-F | 5-CH3 | 2-OCF3 phenyl | 4-F |
| 5-CH3 | 3-CF3 phenyl | 4-F | 5-CH3 | 3-OSO2CH3 phenyl | 4-F |
| 5-CH3 | 3-OCF3 phenyl | 4-F | 5-CH3 | 3-OCF2H phenyl | 4-F |
| 5-CH3 | 3-SCF3 phenyl | 4-F | 5-CH3 | 4-F-3-CF3 phenyl | 4-F |

In addition, the following compounds of formula (Ib) below form part of the present invention:

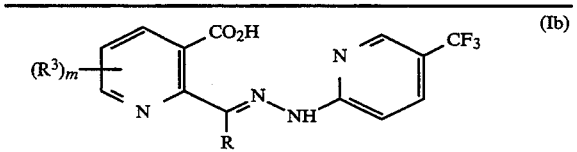

(Ib)

| $(R^3)_m$ | R | $(R^3)_m$ | R |
|---|---|---|---|
| — | 3-CN phenyl | 5-Cl | 3-CN phenyl |
| — | 3-CF3 phenyl | 5-Cl | 3-CF3 phenyl |
| — | 3-OCF3 phenyl | 5-Cl | 3-OCF3 phenyl |
| — | 3-SCF3 phenyl | 5-Cl | 3-SCF3 phenyl |
| — | 2,3-OCF2O- phenyl | 5-Cl | 2,3-OCF2O- phenyl |
| — | 2-OCF3 phenyl | 5-Cl | 2-OCF3 phenyl |
| — | 3-OSO2CH3 phenyl | 5-Cl | 3-OSO2CH3 phenyl |
| — | 3-OCF2H phenyl | 5-Cl | 3-OCF2H phenyl |
| — | 4-F-3-CF3 phenyl | 5-Cl | 4-F-3-CF3 phenyl |
| 5-F | 3-CN phenyl | 5-CH3 | 3-CN phenyl |
| 5-F | 3-CF3 phenyl | 5-CH3 | 3-CF3 phenyl |
| 5-F | 3-OCF3 phenyl | 5-CH3 | 3-OCF3 phenyl |
| 5-F | 3-SCF3 phenyl | 5-CH3 | 3-SCF3 phenyl |
| 5-F | 2,3-OCF2O- phenyl | 5-CH3 | 2,3-OCF2O- phenyl |
| 5-F | 2-OCF3 phenyl | 5-CH3 | 2-OCF3 phenyl |
| 5-F | 3-OSO2CH3 phenyl | 5-CH3 | 3-OSO2CH3 phenyl |
| 5-F | 3-OCF2H phenyl | 5-CH3 | 3-OCF2H phenyl |
| 5-F | 4-F-3-CF3 phenyl | 5-CH3 | 4-F-3-CF3 phenyl |

Compounds of formula I may be prepared by the application or adaptation of known methods (i.e. methods heretofore used or described in the literature), for example as hereinafter described.

In the following description, where symbols appearing in formulae are not specifically defined, it is to be understood that they are "as hereinbefore defined" in accordance with the first definition of each symbol in the specification.

It is to be understood that in the description of the following processes the sequences may be performed in different orders, and that suitable protecting groups may be required to achieve the compounds sought.

According to a feature of the present invention compounds of formula I may be prepared by the reaction of a compound of formula II with a hydrazine of formula III or a salt thereof:

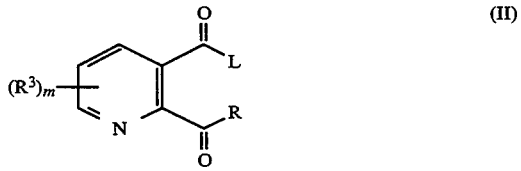

(II)

$R^1R^2N-NH_2$ (III)

wherein R, $R^1$, $R^2$, $R^3$, L and m are as hereinbefore defined. The reaction is generally performed in a solvent such as ethanol or methanol optionally in the presence of a base, for example triethylamine or potassium carbonate (the presence of a base is particularly preferred where a salt of formula III is used) and a catalyst, for example para-toluene sulphonic acid. The reaction is generally carried out at a temperature from $-20°$ C. to the reflux temperature of the solvent.

Compounds of formula II may be prepared by the oxidation of a compound of formula IV:

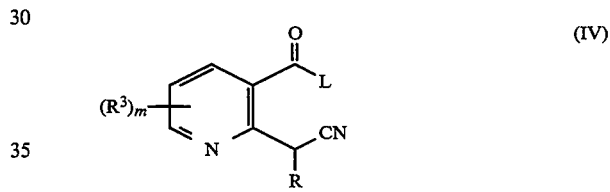

(IV)

wherein R, $R^3$, L and m are as hereinbefore defined, to convert the cyano-methylene group to a carbonyl group. The reaction is carried out in the presence of a base, for example lithium diisopropylamide, potassium carbonate or sodium hydride, in an anhydrous solvent, for example dimethyl sulphoxide, 1,4-dioxan, tetrahydrofuran (THF) or acetonitrile at temperatures from $-72°$ C. to the reflux temperature of the mixture. Generally the oxidant used is air or oxygen.

Alternatively, the reaction may be carried out in a two-phase system comprising an organic solvent such as toluene or dichloromethane and an aqueous solution of a base, for example sodium hydroxide, in the presence of a quaternary ammonium salt, for example triethyl benzylammonium chloride. Generally the oxidant used is air or oxygen. The reaction is generally performed at a temperature from room temperature to the reflux temperature of the mixture.

Compounds of formula II in which L is a straight- or branched- chain alkoxy group containing up to six carbon atoms and R is hydrogen may also be prepared by the reduction of the corresponding pyridine dicarboxylates in which R is replaced by —OH, for example as described by Queguiner et al., Bull. Soc. Chim. Fr., 1969, 3678.

Compounds of formula II in which L is an alkoxy group or an amino group —$NR^7R^8$ may be prepared from the corresponding carboxylic acid of formula II in which L represents —OH by the application or modification of known methods.

Compounds of formula IV may be prepared by the reaction between a nicotinic acid derivative of formula V and a nitrile of formula VI:

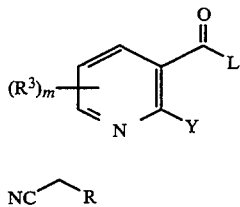

wherein R, $R^3$, L and m are as hereinbefore defined and Y is a leaving group, for example halogen. The reaction is performed in the presence of a base, for example sodium hydride, sodium amide or an alkali metal alkoxide in a solvent, for example toluene, 1,4-dioxan or THF, at temperatures between 0° C. and the reflux temperature of the solvent. The reaction is optionally performed in the presence of a phase transfer catalyst, for example tris[2-(2-methoxyethoxy)ethyl]amine (commonly known as TDA-1). The reaction is particularly useful for preparing compounds of formula (IV) in which L is hydroxy.

Compounds of formula IV in which R represents a straight- or branched- chain alkyl, alkenyl or alkynyl group containing up to six carbon atoms optionally substituted by one or more halogen atoms, —[$CR^{41}R^{42}$]$_n$-(phenyl)-($R^{31}$)$_q$ or —($CR^{41}R^{41}$)$_n$-Het1 wherein n is one or two, may be prepared by the reaction of a 2-cyanomethylnicotinic acid derivative of formula VII with a compound of formula VIII:

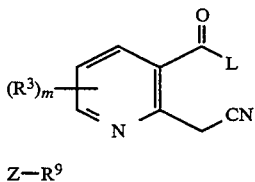

wherein $R^3$, L and m are as hereinbefore defined and $R^9$ represents a straight- or branched- chain alkyl, alkenyl or alkynyl group containing up to six carbon atoms optionally substituted by one or more halogen atoms, —[$CR^{41}R^{42}$]$_n$-(phenyl)-($R^{31}$)$_q$ or —($CR^{41}R^{42}$)$_n$-Het1 wherein n is one or two, and Z is a leaving group, for example halogen or tosyl. The reaction is performed in the presence of a base and is widely described in the literature (for example, as described by Masuyama et al., Chem. Lett., 1977, 1439).

Compounds of formula VII may be prepared by the cyanation of a compound of formula IX:

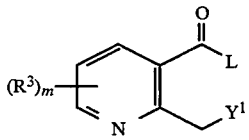

wherein $R^3$, L and m are as hereinbefore defined, and $Y^1$ is a leaving group, for example chlorine or bromine and the cyanide source is, for example sodium cyanide. The reaction is conducted in a solvent, for example aqueous ethanol at a temperature between room temperature and the reflux temperature of the solvent mixture.

Compounds of formula IX in which $Y^1$ represents a halogen atom, for example a chlorine or bromine atom, may be prepared by the halogenation of a methylpyridine compound of formula X:

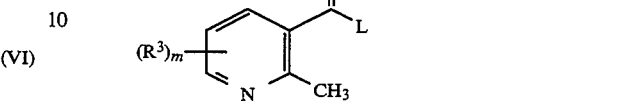

wherein $R^3$, L and m are as hereinbefore defined. The reaction is generally performed in the presence of a suitable halogen source, for example N-chloro- or N-bromosuccinimide in a solvent, for example carbon tetrachloride or chloroform at a temperature between room temperature and the reflux temperature of the solvent. The reaction is preferably conducted in the presence of a reaction initiator, for example benzoyl peroxide.

The hydrazines of formula III, the nitriles of formula VI and the compounds of formulae V, VIII and X are known or may be prepared by the application or modification of known methods.

The following Examples illustrate the preparation of compounds of the formula I and the Reference Example illustrates the preparation of intermediates. In the present specification m.p. means melting point. Unless otherwise stated percentages are by weight.

EXAMPLE 1

The preparation of 2-(3-trifluoromethylbenzoyl)nicotinic acid (4-trifluoromethylphenyl)hydrazone, compound 1

2-(3-Trifluoromethylbenzoyl)nicotinic acid (0.5 g), 4-trifluoromethylphenylhydrazine (0.3 g) and para-toluene sulphonic acid (0.001 g) were stirred in methanol at room temperature for 22 hours. Solvent was evaporated. The residue was triturated in cold toluene then dried to yield the title compound as a beige solid (0.62 g), m.p. 127°–129° C.

By proceeding in a similar manner N,N-dimethyl-2-(3-trifluoromethylbenzoyl)nicotinamide 4-(trifluoromethylphenyl)hydrazone; (Compound 8) was prepared, m.p. 180°–183° C.

By proceeding in a similar manner, under slightly modified conditions (no para-toluenesulphonic acid used; reaction temperatures from 0° C. to room temperature), the following compounds were also prepared:

2-( 3-trifluoromethoxybenzoyl)nicotinic acid (4-trifluoromethylphenyl)hydrazane; (Compound 3), m.p. 87°–89° C.;

2-(3-trifluoromethylbenzoyl)nicotinic acid (4-fluorophenyl)hydrazone (Compound 4), NMR (DMSO-$d_6$): 7.0–7.15(m,2H), 7.15–7.3(m,2H), 7.35–7.9(m,5H), 8.5(dd, 1H), 9.0(dd, 1H), 9.3(s, 1H);

2-(3-trifluoromethylbenzoyl)nicotinic acid (N-methyl-N-phenyl)hydrazone (Compound 5), m.p. 216.2°–216.4° C.;

5-methyl-2-(3-trifluoromethoxybenzoyl)nicotinic acid (4-trifluoromethylphenyl)hydrazone (Compound 6), m.p. 98°–102° C.;

2-(2,3-difluoromethylenedioxybenzoyl)nicotinic acid (4-fluorophenyl)hydrazone (Compound 7), NMR (CDCl$_3$) 7.15–7.30(m,5H), 7.55(dd, 1H), 7.7–7.85(m,3H), 8.87(dd, 1H), 9.12(m, 1H).

EXAMPLE 2

The preparation of 2-(3-trifluoromethylbenzoyl)nicotinic acid (2,6-dichloro-4-trifluoromethylphenyl)hydrazone, compound 2

A suspension of 2-(3-trifluoromethylbenzoyl)nicotinic acid (1.5 g) and 2,6-dichloro-4-trifluoromethylphenylhydrazine (1.87 g) in toluene was stirred at reflux with azeotropic removal of water (using a Dean Stark apparatus) for 6.5 hours. The mixture was cooled to room temperature and then washed with 2N hydrochloric acid and water. The organic phase was dried and evaporated. The crude product was purified by column chromatography to yield a yellow gum which was triturated in hexane to yield the title compound as a pale yellow solid (0.24 g), m.p. 92°–96° C.

REFERENCE EXAMPLE 1

The preparation Of N,N-dimethyl-2-(3-trifluoromethylbenzoyl) nicotinamide (i) A mixture of 2-(3-trifluoromethylbenzoyl)nicotinic acid (1.8 g) and thionyl chloride (10 ml) was heated at reflux for 3.5 hours. Excess reagent was removed by evaporation to yield 2-(3-trifluoromethylbenzoyl)nicotinoyl chloride as a red-brown gum (2 g) which was used in the next step without further purification.

(ii) The product from step (i) above was dissolved in dry toluene (10 ml). Dimethylamine hydrochloride (1.3 g) was added followed by triethylamine (1.94 g). The mixture was then stirred at room temperature for 4.5 hours. The mixture was diluted with ethyl acetate and washed successively with ethyl acetate and washed successively with 2N sodium carbonate, 2N hydrochloric acid then water. The organic phase was dried then evaporated to yield a red-brown gum which was triturated in hexane to yield the title product as a beige solid (0.64 g), m.p.100°–103° C.

REFERENCE EXAMPLE 2

The preparation of 2-(3-trifluoromethylbenzoyl)nicotinic acid

A solution of 3-(trifluoromethyl)phenylacetonitrile (50 g) in dry 1,4-dioxan was added to a stirred suspension of sodium hydride (80% oil dispersion; 24.6 g) in dry 1,4-dioxan. The mixture was stirred at room temperature for 15 minutes. A solution of 2-chloronicotinic acid (39.4 g) in dry 1,4-dioxan was added over a period of 5–10 minutes. The resulting mixture was stirred at room temperature for 15 minutes and then at the reflux temperature for 3.5 hours.

The mixture was cooled to 80° C. Air was bubbled rapidly into the stirred suspension over a period of 2.5 hours maintaining the temperature at 65°–70° C. The reaction mixture was allowed to stand at room temperature overnight. Introduction of air was then recommenced and maintained for a period of 7 hours, with the reaction mixture being stirred at 65°–70° C.

The cooled mixture was poured carefully into ice/water and the mixture washed with diethyl ether. The aqueous phase was acidified to pH 3 with hydrochloric acid and extracted with ethyl acetate. The combined organic extracts were washed with water, dried and evaporated. The crude material then obtained was triturated successively with hexane, chloroform then hot toluene to yield the title compound as a cream solid (30.2 g), m.p. 209°–210° C.

By proceeding in a similar manner, the following compounds were also prepared:

2-(3-trifluoromethoxybenzoyl)nicotinic acid, m.p. 147°–150° C.;

5-methyl-2-(3-trifluoromethoxybenzoyl)nicotinic acid, m.p. 134°–138° C.;

2-(2,3-difluoromethylenedioxybenzoyl)nicotinic acid, NMR (CDCl$_3$), 7.08–7.25(m,2H), 7.45–7.58(m,2H), 8.36(dd, 1H), 8.73(m, 1H).

REFERENCE EXAMPLE 3

Preparation of 2,3-difluoromethylenedioxybenzyl cyanide 2,3-Difluoromethylenedioxybenzyl bromide (40.4 g) was dissolved in ethanol and potassium cyanide (11.3 g) was added. The mixture was stirred at 70° C. for 5 hours. Water and a further portion of potassium cyanide (2 g) were added and the mixture was stirred at 70° C. for a further 3 hours. Most of the solvent was removed in vacuo and water was added to the residue, which was extracted with diethyl ether, washed with water, dried and concentrated to yield the title compound as a yellow oil, (30.2 g), NMR (CDCl$_3$): 3.80(s,2H), 7.10(m,3H).

REFERENCE EXAMPLE 4

Preparation of 2,3-difluoromethylenedioxybenzyl bromide

Phosphorus tribromide (47 g) was added to a solution of 2,3difluoromethylenedioxybenzyl alcohol (32 g) in diethyl ether at 0° C. After 0.5 hours the reaction mixture was allowed to warm to ambient temperature and was stirred at ambient temperature for 3 hours. The reaction mixture was then cooled to 0° C., methanol was added followed by water, the mixture was extracted with diethyl ether, separated and the organic layer washed with saturated sodium bicarbonate (until neutral), dried and the solvent removed to yield the product as a pale yellow oil, (40.4 g), NMR (CDCl$_3$): 4.50(s,2H), 7.10(m,3H).

REFERENCE EXAMPLE 5

Preparation of 2,3-difluoromethylenedioxybenzyl alcohol

A solution of sodium borohydride (5 g) in methanol was added to a solution of 2,3-difluoromethylenedioxybenzaldehyde (36 g) in methanol with cooling so that the temperature did not exceed 10 ° C. The reaction mixture was then allowed to warm to ambient temperature and stirred for 1 hour. Most of the methanol was evaporated and the residue was poured into cold 20% sodium hydroxide solution, extracted with ether, separated and washed with brine (until neutral), dried and the solvent removed to yield the title compound as a colourless oil (33.7 g), NMR (CDCl$_3$): 2.10(br, 1H), 4.80(d,2H), 7.00(m, 1H), 7.10(m,2H).

REFERENCE EXAMPLE 6

The preparation Of 2,3-Difluoromethylenedioxybenzaldehyde

A solution of n-butyllithium (2.5M in hexane; 88 ml) was added dropwise to a stirred, cooled (−78° C.) solution of 2,3-difluoromethylenedioxybenzene (31.6 g) in dry tetrahydrofuran (200 ml). The reaction temperature was kept at −70° C. or below throughout the addition. The resulting mixture was stirred at −70° C. to −78° C. for 3 hours.

Dimethylformamide (36 ml) was then added dropwise, maintaining the reaction temperature at −65° C. or below. When the addition was complete, the mixture was allowed to warm to −10° C. and then stirred at that temperature for 45 minutes. 1N Hydrochloric acid (50 ml) was added and the mixture was stirred vigorously for 15 minutes then poured into water.

The mixture was extracted with ethyl acetate. The extracts were combined, washed with brine, dried and evaporated to yield the title product as a clear oil (37.2 g), NMR (CDCl$_3$); 7.15–7.35 (m,2H), 7.57(dd, 1H), 10.2(5,1H).

REFERENCE EXAMPLE 7

The preparation Of 2-chloro-5-methylnicotinic acid

An aqueous solution of sodium hydroxide (9.2 g) was added to an ice-cooled, stirred solution of methyl 2-chloro-5-methylnicotinoate (35.28 g) in methanol at such a rate so that the temperature of the reaction mixture did not exceed 30° C. The mixture was then stirred at room temperature for 1.5 hours. Solvent was evaporated. The residue was diluted with water and acidified to pH 2 with concentrated hydrochloric acid. The precipitate was collected by filtration, washed with water and dried to yield the title compound as a pale yellow solid, 31.92 g, m.p. 180°–180.5° C.

REFERENCE EXAMPLE 8

The preparation of methyl 2-chloro-5-methylnicotinoate

Hydrogen chloride gas was bubbled through a suspension of methyl 5-(N,N-dimethylamino )-2-cyano-4-methylpent-2,4-dienoate (37.4 g) in 1,2-dichloroethane for 6 hours. Further saturation of the suspension with HCl gas was followed by stirring at room temperature overnight. Excess HCl was blown out of the reaction mixture with nitrogen gas. The mixture was washed with water, dried and evaporated. The resulting oil crystallised on standing to yield the title compound as orange crystals, 35.28 g, NMR(CDCl$_3$) d=2.25 (s,3H,CH$_3$), 3.85(s,3H,CO$_2$CH$_3$), 7.85 (d, 1H), 8.23 (d, 1H).

REFERENCE EXAMPLE 9

The preparation of methyl 5-(N,N-dimethylamino)-2-cyano-4-methylpent-2,4-dienoate A solution of oxalyl chloride (83.2 g) in 1,2-dichloroethane was added dropwise to a stirred, cooled (0° C.) solution of dimethylformamide (109.5 g) in 1,2-dichloroethane so that the temperature of the reaction mixture did not exceed 10° C. The resulting mixture was stirred at 0°–5° C. for a further 1.75 hours then allowed to reach room temperature. 2-Methylmalonic acid (35.4 g) was added to the stirred mixture. When gas evolution had ceased, the mixture was stirred at the reflux temperature for 6 hours then at room temperature overnight. Solvent was evaporated (keeping bath temperature at 25° C. or less) and replaced with dry methanol. Methyl cyanoacetate (32.7 g) was added and the mixture was stirred. Sodium methoxide (53.5 g) was then added ensuring that the reaction mixture temperature did not exceed 30° C. The cooled mixture was stirred for a further 30 minutes then at room temperature for 3.5 hours. Solvent was removed by evaporation and replaced with dichloromethane. The mixture was then washed with water, dried and evaporated. The crude product was triturated with cold methanol to yield the title compound as a yellow crystalline solid, 37.44 g, m.p. 167.5°–168.5° C.

According to a feature of the present invention, there is provided a method for controlling the growth of weeds (i.e. undesired vegetation) at a locus which comprises applying to the locus a herbicidally effective amount of at least one nicotinic acid hydrazone derivative of formula I or an agriculturally acceptable salt thereof. For this purpose, the nicotinic acid hydrazones are normally used in the form of herbicidal compositions (i.e. in association with compatible diluents or carriers and/or surface active agents suitable for use in herbicidal compositions), for example as hereinafter described.

The compounds of formula I show herbicidal activity against dicotyledonous (i.e. broad-leafed) and monocotyledonous (e.g. grass) weeds by pre- and/or post-emergence application.

By the term "pre-emergence application" is meant application to the soil in which the weed seeds or seedlings are present before emergence of the weeds above the surface of the soil. By the term "post-emergence application" is meant application to the aerial or exposed portions of the weeds which have emerged above the surface of the soil. For example, the compounds of formula I may be used to control the growth of:

broad-leafed weeds, for example, *Abutilon theophrasti, Amaranthus retroflexus, Bidens pilosa, Chenopodium album, Galium aparine,* Ipomoea spp. e.g. *Ipomoea purpurea, Sesbania exaltata, Sinapis arvensis, Solanum nigrum* and *Xanthium strumarium,* and grass weeds, for example *Alopecurus myosuroides, Avena fatua, Digitaria sanguinalis, Echinochloa crus-galli, Eleusine indica* and Setaria spp, e.g. *Setaria faberii* or *Setaria viridis,* and sedges, for example, *Cyperus esculentus.*

The amounts of compounds of formula I applied vary with the nature of the weeds, the compositions used, the time of application, the climatic and edaphic conditions and (when used to control the growth of weeds in crop-growing areas) the nature of the crops. When applied to a crop-growing area, the rate of application should be sufficient to control the growth of weeds without causing substantial permanent damage to the crop. In general, taking these factors into account, application rates between 0.01 kg and 5 kg of active material per hectare give good results. However, it is to be understood that higher or lower application rates may be used, depending upon the particular problem of weed control encountered.

The compounds of formula I may be used to control selectively the growth of weeds, for example to control the growth of those species hereinbefore mentioned, by pre- or post-emergence application in a directional or non-directional fashion, e.g. by directional or non-directional spraying, to a locus of weed infestation which is an area used, or to be used, for growing crops, for example cereals, e.g. wheat, barley, oats, maize and rice, soya beans, field and dwarf beans, peas, lucerne, cotton, peanuts, flax, onions, carrots, cabbage, oilseed rape, sunflower, sugar beet, and permanent or sown grassland before or after sowing of the crop or before or after emergence of the crop. For the selective control of weeds at a locus of weed infestation which is an area used, or to be used, for growing of crops, e.g. the crops hereinbefore mentioned, application rates between 0.01 kg and 4.0 kg, and preferably between 0.01 kg and 2.0 kg, of active material per hectare are particularly suitable.

The compounds of formula I may also be used to control the growth of weeds, especially those indicated above, by pre- or post-emergence application in established orchards and other tree-growing areas, for example forests, woods and parks, and plantations, e.g. sugar cane, oil palm and rubber plantations. For this purpose they may be applied in a directional or non-directional fashion (e.g. by directional or non-directional spraying) to the weeds or to the soil in which they are expected to appear, before or after planting of the trees or plantations at application rates between 0.25 kg and 5.0 kg, and preferably between 0.5 kg and 4.0 kg of active material per hectare.

The compounds of formula I may also be used to control the growth of weeds, especially those indicated above, at loci which are not crop-growing areas but in which the control of weeds is nevertheless desirable.

Examples of such non-crop-growing areas include airfields, industrial sites, railways, roadside verges, the verges of rivers, irrigation and other waterways, scrublands and fallow or uncultivated land, in particular where it is desired to control the growth of weeds in order to reduce fire risks. When used for such purposes in which a total herbicidal effect is frequently desired, the active compounds are normally applied at dosage rates higher than those used in crop-growing areas as hereinbefore described. The precise dosage will depend upon the nature of the vegetation treated and the effect sought.

Pre- or post-emergence application, and preferably pre-emergence application, in a directional or non-directional fashion (e.g. by directional or non-directional spraying) at application rates between 1.0 kg and 20.0 kg, and preferably between 5.0 and 10.0 kg, of active material per hectare are particularly suitable for this purpose.

When used to control the growth of weeds by pre-emergence application, the compounds of formula I may be incorporated into the soil in which the weeds are expected to emerge. It will be appreciated that when the compounds of formula I are used to control the growth of weeds by post-emergence application, i.e. by application to the aerial or exposed portions of emerged weeds, the compounds of formula I will also normally come into contact with the soil and may also then exercise a pre-emergence control on later-germinating weeds in the soil.

Where especially prolonged weed control is required, the application of the compounds of formula I may be repeated if required.

According to a further feature of the present invention, there are provided compositions suitable for herbicidal use comprising one or more of the nicotinic acid hydrazones of formula I or an agriculturally acceptable salt thereof, in association with, and preferably homogeneously dispersed in, one or more compatible agriculturally-acceptable diluents or carriers and/or surface active agents [i.e. diluents or carriers and/or surface active agents of the type generally accepted in the an as being suitable for use in herbicidal compositions and which are compatible with compounds of formula I]. The term "homogeneously dispersed" is used to include compositions in which the compounds of formula I are dissolved in other components. The term "herbicidal compositions" is used in a broad sense to include not only compositions which are ready for use as herbicides but also concentrates which must be diluted before use. Preferably, the compositions contain from 0.05 to 90% by weight of one or more compounds of formula I.

The herbicidal compositions may contain both a diluent or carrier and surface-active (e.g. wetting, dispersing, or emulsifying) agent. Surface-active agents which may be present in herbicidal compositions of the present invention may be of the ionic or non-ionic types, for example sulphoricinoleates, quaternary ammonium derivatives, products based on condensates of ethylene oxide with alkyl and polyaryl phenols, e.g. nonyl- or octyl-phenols, or carboxylic acid esters of anhydrosorbitols which have been rendered soluble by etherification of the free hydroxy groups by condensation with ethylene oxide, alkali and alkaline earth metal salts of sulphuric acid esters and sulphonic acids such as dinonyl- and dioctyl-sodium sulphonosuccinates and alkali and alkaline earth metal salts of high molecular weight sulphonic acid derivatives such as sodium and calcium lignosulphonates and sodium and calcium alkylbenzene sulphonates.

Suitably, the herbicidal compositions according to the present invention may comprise up to 10% by weight, e.g. from 0.05% to 10% by weight, of surface-active agent but, if desired, herbicidal compositions according to the present invention may comprise higher proportions of surface-active agent, for example up to 15% by weight in liquid emulsifiable suspension concentrates and up to 25% by weight in liquid water soluble concentrates.

Examples of suitable solid diluents or carriers are aluminium silicate, talc, calcined magnesia, kieselguhr, tricalcium phosphate, powdered cork, absorbent carbon black and clays such as kaolin and bentonite. The solid compositions (which may take the form of dusts, granules or wettable powders) are preferably prepared by grinding the compounds of formula I with solid diluents or by impregnating the solid diluents or carriers with solutions of the compounds of formula I in volatile solvents, evaporating the solvents and, if necessary, grinding the products so as to obtain powders. Granular formulations may be prepared by absorbing the compounds of formula I (dissolved in suitable solvents, which may, if desired, be volatile) onto the solid diluents or carriers in granular form and, if desired, evaporating the solvents, or by granulating compositions in powder form obtained as described above. Solid herbicidal compositions, particularly wettable powders and granules, may contain wetting or dispersing agents (for example of the types described above), which may also, when solid, serve as diluents or carriers.

Liquid compositions according to the invention may take the form of aqueous, organic or aqueous-organic solutions, suspensions and emulsions which may incorporate a surface-active agent. Suitable liquid diluents for incorporation in the liquid compositions include water, glycols, tetrahydrofurfuryl alcohol, acetophenone, cyclohexanone, isophorone, toluene, xylene, mineral, animal and vegetable oils and light aromatic and naphthenic fractions of petroleum (and mixtures of these diluents). Surface-active agents, which may be present in the liquid compositions, may be ionic or non-ionic (for example of the types described above) and may, when liquid, also serve as diluents or carriers.

Powders, dispersible granules and liquid compositions in the form of concentrates may be diluted with water or other suitable diluents, for example mineral or vegetable oils, particularly in the case of liquid concentrates in which the diluent or carrier is an oil, to give compositions ready for use.

When desired, liquid compositions of the compound of formula I may be used in the form of self-emulsifying concentrates containing the active substances dissolved in the emulsifying agents or in solvents containing emulsifying agents compatible with the active substances, the simple addition of water to such concentrates producing compositions ready for use.

Liquid concentrates in which the diluent or carrier is an oil may be used without further dilution using the electrostatic spray technique.

Herbicidal compositions according to the present invention may also contain, if desired, conventional adjuvants such as adhesives, protective colloids, thickeners, penetrating agents, stabilisers, sequestering agents, anti-caking agents, colouring agents and corrosion inhibitors. These adjuvants may also serve as carriers or diluents.

Unless otherwise specified, the following percentages are by weight. Preferred herbicidal compositions according to the present invention are:

aqueous suspension concentrates which comprise from 10 to 70% of one or more compounds of formula I, from 2 to 10% of surface-active agent, from 0.1 to 5% of thickener and from 15 to 87.9% of water;

wettable powders which comprise from 10 to 90% of one or more compounds of formula I, from 2 to 10% of surface-active agent and from 8 to 88% of solid diluent or carrier;

water soluble or water dispersible powders which comprise from 10 to 90% of one or more compounds of formula I, from 2 to 40% of sodium carbonate and from 0 to 88% of solid diluent;

liquid water soluble concentrates which comprise from 5 to 50%, e.g. 10 to 30%, of one or more compounds of formula I, from 5 to 25% of surface-active agent and from 25 to 90%, e.g. 45 to 85%, of water miscible solvent, e.g. dimethylformamide, or a mixture of water-miscible solvent and water;

liquid emulsifiable suspension concentrates which comprise from 10 to 70% of one or more compounds of formula I, from 5 to 15% of surface-active agent, from 0.1 to 5% of thickener and from 10 to 84.9% of organic solvent;

granules which comprise from 1 to 90%, e.g. 2 to 10% of one or more compounds of formula I, from 0.5 to 7%, e.g. 0.5 to 2%, of surface-active agent and from 3 to 98.5%, e.g. 88 to 97.5%, of granular carrier and emulsifiable concentrates which comprise 0.05 to 90%, and preferably from 1 to 60% of one or more compounds of formula I, from 0.01 to 10%, and preferably from 1 to 10%, of surface-active agent and from 9.99 to 99.94%, and preferably from 39 to 98.99%, of organic solvent.

Herbicidal compositions according to the present invention may also comprise the compounds of formula I in association with, and preferably homogeneously dispersed in, one or more other pesticidally active compounds and, if desired, one or more compatible pesticidally acceptable diluents or carriers, surface-active agents and conventional adjuvants as hereinbefore described.

Pesticidally active compounds and other biologically active materials which may be included in, or used in conjunction with, the herbicidal compositions of the present invention, for example those hereinbefore mentioned, and which are acids, may, if desired, be utilized in the form of conventional derivatives, for example alkali metal and amine salts and esters.

The following Examples illustrate herbicidal compositions according to the present invention:

EXAMPLE C1

A soluble concentrate is formed from:

| | |
|---|---|
| Active ingredient (compound 1) | 20% w/v |
| Potassium hydroxide solution 33% w/v | 10% v/v |
| Tetrahydrofurfuryl alcohol (THFA) | 10% v/v |
| Water | to 100 volumes. | by stirring THFA, active ingredient (compound 1) and 90% volume of water and slowly adding the potassium hydroxide solution until a steady pH 7–8 is obtained, then making up to volume with water.

Similar soluble concentrates may be prepared as described above by replacing the nicotinic acid hydrazone (compound 1) with other compounds of formula I.

EXAMPLE C2

A wettable powder is formed from:

| | |
|---|---|
| Active ingredient (compound 1) | 50% w/w |
| Sodium dodecylbenzene sulphonate | 3% w/w |
| Sodium lignosulphate | 5% w/w |
| Sodium formaldehyde alkylnaphthalene sulphonate | 2% w/w |
| Microfine silicon dioxide | 3% w/w |
| China clay | 37% w/w | by blending the above ingredients together and grinding the mixture in an air jet mill.

Similar wettable powders may be prepared as described above. by replacing the nicotinic acid hydrazone (compound 1 ) with other compounds of formula I.

EXAMPLE C3

A water soluble powder is formed from:

| | |
|---|---|
| Active ingredient (compound 1) | 50% w/w |
| Sodium dodecylbenzenesulphonate | 1% w/w |
| Microfine silicon dioxide | 2% w/w |
| Sodium bicarbonate | 47% w/w | by mixing the above ingredients and grinding the above mixture in a hammer mill.

Similar water soluble powders may be prepared as described above by replacing the nicotinic acid hydrazone (compound 1) with other compounds of formula I.

Representative compounds of formula I have been used in herbicidal applications according to the following procedures.

METHOD OF USE OF HERBICIDAL COMPOUNDS a) General

Appropriate quantities of the compounds used to treat the plants were dissolved in acetone to give solutions equivalent to application rates of up to 4000 g test compound per hectare (g/ha). These solutions were applied from a standard laboratory herbicide sprayer delivering the equivalent of 290 liters of spray fluid per hectare.

b) Weed Control: Pre-Emergence

The seeds were sown in 70 mm square, 75 mm deep plastic pots in non-sterile soil. The quantities of seed per pot were as follows:

|  | Approx number of seeds/pot |
|---|---|
| Weed species | |
| 1) Broad-leafed weeds | |
| Abutilon theophrasti | 10 |
| Amaranthus retroflexus | 20 |
| Galium aparine | 10 |
| Ipomoea purpurea | 10 |
| Sinapis arvensis | 15 |
| Xanthium strumarium | 2. |
| 2) Grass weeds | |
| Alopecurus myosuroides | 15 |
| Avena fatua | 10 |
| Echinochloa crus-galli | 15 |
| Setaria viridis | 20. |
| 3) Sedges | |
| Cyperus esculentus | 3. |
| Crop | |
| 1) Broad-leafed | |
| Cotton | 3 |
| Soya | 3. |
| 2) Grass | |
| Maize | 2 |
| Rice | 6 |
| Wheat | 6. |

The compounds of the invention were applied to the soil surface, containing the seeds, as described in (a). A single pot of each crop and each weed was allocated to each treatment, with unsprayed controls and controls sprayed with acetone alone.

After treatment the pots were placed on capillary matting kept in a glass house, and watered overhead. Visual assessment of crop damage was made 20–24 days after spraying. The results were expressed as the percentage reduction in growth or damage to the crop or weeds, in comparison with the plants in the control pots.

c) Weed Control: Post-Emergence

The weeds and crops were sown directly into John Innes potting compost in 75 mm deep, 70 mm square pots except for Amaranthus which was pricked out at the seedling stage and transferred to the pots one week before spraying. The plants were then grown in the greenhouse until ready for spraying with the compounds used to treat the plants. The number of plants per pot were as follows:

| Weed species | Number of plants per pot | Growth stage |
|---|---|---|
| 1) Broad leafed weeds | | |
| Abutilon theophrasti | 3 | 1–2 leaves |
| Amaranthus retroflexus | 4 | 1–2 leaves |
| Galium aparine | 3 | 1st whorl |
| Ipomoea purpurea | 3 | 1–2 leaves |
| Sinapis arvensis | 4 | 2 leaves |
| Xanthium strumarium | 1 | 2–3 leaves. |
| 2) Grass weeds | | |
| Alopecurus myosuroides | 8–12 | 1–2 leaves |
| Avena fatua | 12–18 | 1–2 leaves |
| Echinochloa crus-galli | 4 | 2–3 leaves |
| Setaria viridis | 15–25 | 1–2 leaves. |
| 3) Sedges | | |
| Cyperus esculentus | 3 | 3 leaves. |

| Crops | Number of plants per pot | Growth stage |
|---|---|---|
| 1) Broad leafed | | |
| Cotton | 2 | 1 leaf |
| Soya | 2 | 2 leaves. |
| 2) Grass | | |
| Maize | 2 | 2–3 leaves |
| Rice | 4 | 2–3 leaves |
| Wheat | 5 | 2–3 leaves. |

The compounds used to treat the plants were applied to the plants as described in (a). A single pot of each crop and weed species was allocated to each treatment, with unsprayed controls and controls sprayed with acetone alone.

After treatment the pots were placed on capillary matting in a glass house, and watered overhead once after 24 hours and then by controlled sub-irrigation. Visual assessment of crop damage and weed control was made 20–24 days after spraying. The results were expressed as the percentage reduction in growth or damage to the crop or weeds, in comparison with the plants in the control pots.

When applied at 1000 g/hectare pre- or post-emergence, compounds 1, 2, 3 and 8 gave at least 90% reduction in growth of one or more weed species.

While the invention has been described in terms of various preferred embodiments, the skilled artisan will appreciate that various modifications, substitutions, omissions and changes may be made without departing from the spirit thereof. Accordingly, it is intended that the scope of the present invention be limited solely by the scope of the following claims, including equivalents thereof.

What is claimed is:

1. A compound of the formula:

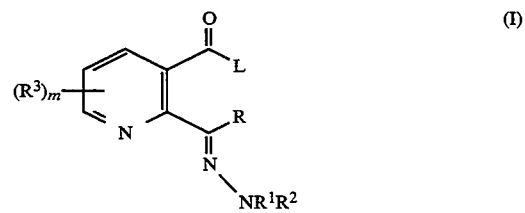

wherein:

R represents:
hydrogen;
straight- or branched-chain alkyl, alkenyl or alkynyl having up to six carbon atoms, optionally substituted by one or more halogen;
Het;
—[CR$^{41}$R$^{42}$]$_n$-Het1; or
—[CR$^{41}$R$^{42}$]$_n$-(phenyl)-(R$^{31}$)$_p$;

R$^1$ represents:
hydrogen;
straight- or branched-chain alkyl, alkenyl or alkynyl having up to six carbon atoms, optionally substituted by one or more halogen;
Het;
—[CR$^{41}$R$^{42}$]$_n$-Het1; or

[CR$^{41}$R$^{42}$]$_n$-(phenyl)-(R$^{32}$)$_q$;

R$^2$ represents:
- hydrogen;
- straight- or branched-chain alkyl, alkenyl or alkynyl having up to six carbon atoms, optionally substituted by one or more halogen; or
- phenyl, optionally substituted by from one to five R$^{31}$ groups, which can be the same or different;

R$^3$ represents:
- halogen;
- straight- or branched-chain alkyl, alkenyl or alkynyl having up to six carbon atoms, optionally substituted by one or more halogen;
- —CN; —CO$_2$R$^4$; —S(O)$_r$R$^4$; —NO$_2$; —NR$^{41}$R$^{42}$; —OH; —COR$^4$; —S(O)$_r$R$^5$; —CO$_2$R$^5$; —OR$^5$; —CONR$^{41}$R$^{42}$; —OSO$_2$R$^5$; —OSO$_2$R$^6$; —OCH$_2$R$^5$; —N(R$^{41}$)COR$^6$; —N(R$^{41}$)SO$_2$R$^5$; —N(R$^{41}$)SO$_2$R$^6$; —SO$_2$NR$^{41}$R$^{42}$; —Si(R$^6$)$_3$;
- phenyl, optionally substituted by from one to five R$^{31}$ groups, which can be the same or different; or
- straight- or branched-chain alkoxy having up to six carbon atoms, optionally substituted by one or more halogen;

L represents:
- hydroxy;
- straight- or branched-chain alkoxy having up to six carbon atoms; or
- —NR$^7$R$^8$;

each of R$^{31}$ and R$^{32}$, which can be the same or different, represents:
- halogen;
- straight- or branched-chain alkoxy having up to six carbon atoms, optionally substituted by one or more halogen;
- straight- or branched-chain alkyl, alkenyl or alkynyl having up to six carbon atoms, optionally substituted by one or more halogen;
- —OH; —S(O)$_r$R$^4$; —CO$_2$R$^4$; —COR$^4$; —CN; —NO$_2$; —NR$^{41}$R$^{42}$; —S(O)$_r$R$^5$; —CO$_2$R$^5$; —OR$^5$; —CONR$^{41}$R$^{42}$; —OSO$_2$R$^5$; —OSO$_2$R$^6$; —OCH$_2$R$^5$; —N(R$^{41}$)COR$^6$; —N(R$^{41}$)SO$_2$R$^5$; —N(R$^{41}$)SO$_2$R$^6$; —SO$_2$NR$^{41}$R$^{42}$; or —Si(R$^6$)$_3$;

R$^4$ represents hydrogen or straight- or branched-chain alkyl having up to six carbon atoms, optionally substituted by one or more halogen;

each of R$^{41}$ and R$^{42}$, which can be the same or different, represents hydrogen or straight- or branched-chain alkyl having up to four carbon atoms, optionally substituted by one or more halogen;

R$^5$ represents phenyl, optionally bearing from one to five substituents, which can be the same or different, selected from the group consisting of halogen, nitro, cyano, R$^4$ and —OR$^4$;

R$^6$ represents straight- or branched-chain alkyl having up to six carbon atoms, optionally substituted by one or more halogen;

each of R$^7$ and R$^8$, which can be the same or different, represents:
- hydrogen;
- straight- or branched-chain alkyl having up to four carbon atoms, optionally substituted by one or more halogen; or
- phenyl, optionally bearing from one to five substituents, which can be the same or different, selected from the group consisting of halogen, nitro, cyano, R$^4$ and —OR$^4$;

Het represents a 5 or 6 membered heterocycle having from 3 to 5 ring carbon atoms and one or more ring heteroatoms selected from the group consisting of nitrogen, oxygen and sulphur, said heterocycle being optionally substituted by one or more R$^{31}$groups, which can be the same or different;

Het1 represents phenyl or a 5 or 6 membered heterocycle having from 3 to 5 ring carbon atoms and one or more ring heteroatoms selected from the group consisting of nitrogen, oxygen and sulphur, wherein two substituents on adjacent positions of the phenyl or heterocyclic ring, together with the two atoms to which they are attached, form a 5- to 7-membered alicyclic ring which is optionally unsaturated or an aromatic ring, the alicyclic or aromatic ring optionally having one or more ring heteroatoms, the phenyl or heterocyclic ring being optionally substituted by one or more R$^{31}$ groups, the alicyclic or aromatic ring being optionally substituted by one or more R$^{51}$ groups, which can be the same or different;

R$^{51}$ is as defined above for R$^{31}$ or represents =O or =S;

m represents zero or an integer from one to three, provided that when m is greater than one, then the R$^3$ groups can be the same or different;

n represents zero, one or two, provided that when n is two, then the —(CR$^{41}$R$^{42}$)— groups can be the same or different;

p represents zero or an integer from one to five, provided that when p is greater than one, then the R$^{31}$ groups can be the same or different;

q represents zero or an integer from one to five, provided that when q is greater than one, then the R$^{32}$ groups can be the same or different; and r represents zero, one or two;

or an agriculturally acceptable salt thereof.

2. A compound according to claim 1, wherein:

R represents:
- hydrogen;
- straight- or branched-chain alkyl, alkenyl or alkynyl having up to six carbon atoms, optionally substituted by one or more halogen;
- Het; or
- —[CR$^{41}$R$^{42}$]$_n$-(phenyl)-(R$^{31}$)$_p$;

R$^1$ represents:
- hydrogen;
- straight- or branched-chain alkyl, alkenyl or alkynyl having up to six carbon atoms, optionally substituted by one or more halogen;
- Het; or
- —[CR$^{41}$R$^{42}$]$_n$-(phenyl)-(R$^{32}$)$_q$;

R$^2$ represents:
- hydrogen;
- straight- or branched-chain alkyl, alkenyl or alkynyl having up to six carbon atoms, optionally substituted by one or more halogen; or
- phenyl, optionally substituted by from one to five R$^{31}$ groups, which can be the same or different;

R$^3$ represents:
- halogen;
- straight- or branched-chain alkyl, alkenyl or alkynyl having up to six carbon atoms, optionally substituted by one or more halogen;
- —CN; —CO$_2$R$^4$; —S(O)$_r$R$^4$; NR$^{41}$R$^{42}$; —OH; —COR$^4$; —S(O)$_r$R$^5$; —CO$_2$R$^5$; —OR$^5$; —CONR$^{41}$R$^{42}$; —OSO$_2$R$^5$; —OSO$_2$R$^6$;

—OCH$_2$R$^5$; —N(R$^{41}$)COR$^6$; —N(R$^{41}$)SO$_2$R$^5$; —N(R$^{41}$)SO$_2$R$^6$; —SO$_2$NR$^{41}$R$^{42}$;

phenyl, optionally substituted by from one to five R$^{31}$ groups, which can be the same or different; or straight- or branched-chain alkoxy having up to six carbon atoms, optionally substituted by one or more halogen;

L represents:
hydroxy;
straight- or branched-chain alkoxy having up to six carbon atoms; or
—NR$^7$R$^8$;

each of R$^{31}$ and R$^{32}$, which can be the same or different, represents:
halogen;
straight- or branched-chain alkoxy having up to six carbon atoms, optionally substituted by one or more halogen;
straight- or branched-chain alkyl, alkenyl or alkynyl having up to six carbon atoms, optionally substituted by one or more halogen;
—OH; —S(O)$_r$R$^4$; —CO$_2$R$^4$; —COR$^4$; —CN; —NO$_2$; —NR$^{41}$R$^{42}$; —S(O)$_4$R$^5$; —CO$_2$R$^5$; —OR$^5$; —CONR$^{41}$R$^{42}$; —OSO$_2$R$^5$; —OSO$_2$R$^6$; —OCH$_2$R$^5$; —N(R$^{41}$)COR$^6$; —N(R$^{41}$)SO$_2$R$^5$; —N(R$^{41}$)SO$_2$R$^6$; or —SO$_2$NR$^{41}$R$^{42}$;

R$^4$ represents hydrogen or straight- or branched-chain alkyl having up to six carbon atoms, optionally substituted by one or more halogen;

each of R$^{41}$ and R$^{42}$, which can be the same or different, represents hydrogen or straight- or branched-chain alkyl having up to four carbon atoms, optionally substituted by one or more halogen;

R$^5$ represents phenyl, optionally bearing from one to five substituents, which can be the same or different, selected from the group consisting of halogen, nitro, cyano, R$^4$ and —OR$^4$;

R$^6$ represents straight- or branched-chain alkyl having up to six carbon atoms, optionally substituted by one or more halogen;

each of R$^7$ and R$^8$ which can be the same or different, represents:
hydrogen;
straight- or branched-chain alkyl having up to four carbon atoms, optionally substituted by one or more halogen; or
phenyl, optionally bearing from one to five substituents, which can be the same or different, selected from the group consisting of halogen, nitro, cyano, R$^4$ and —OR$^4$;

Het represents a 5 or 6 membered heterocycle having from 3 to 5 ring carbon atoms and one or more ring heteroatoms selected from the group consisting of nitrogen, oxygen and sulphur, said heterocycle being optionally substituted by one or more R$^{31}$ groups, which can be the same or different;

m represents zero or an integer from one to three, provided that when m is greater than one, then the R$^3$ groups can be the same or different;

n represents zero, one or two, provided that when n is two, then the —(CR$^{41}$R$^{42}$)— groups can be the same or different;

p represents zero or an integer from one to five, provided that when p is greater than one, then the R$^{31}$ groups can be the same or different;

q represents zero or an integer from one to five, provided that when q is greater than one, then the R$^{32}$ groups can be the same or different; and r represents zero, one or two.

3. A compound according to claim 1, wherein n represents zero.

4. A compound according to claim 1, wherein L represents —NR$^7$R$^8$ or hydroxy.

5. A compound according to claim 1, wherein R$^2$ represents hydrogen.

6. A compound according to claim 3, wherein R represents phenyl substituted in the 3-position by an R$^{31}$ group.

7. A compound according to claim 6, wherein R$^{31}$ is cyano, —OCF$_3$ or —CF$_3$.

8. A compound according to claim 1, wherein R represents a group —(CR$^{41}$R$^{42}$)$_n$-Het1, wherein Het1 represents a phenyl ring having two substituents in the 2- and 3-positions of the phenyl ring which, together with the two atoms to which they are attached, form a 5- or 6-membered alicyclic ring which is optionally unsaturated or an aromatic ring, the alicyclic or aromatic ring having one or two ring heteroatoms selected from oxygen, sulphur and nitrogen, the phenyl ring being optionally substituted by from one to three R$^{31}$ groups, the alicyclic or aromatic ring being optionally substituted by one or more R$^{51}$ groups, which can be the same or different.

9. A compound according to claim 8, wherein R represents —(CR$^{41}$R$^{42}$)$_n$-Het1, wherein n is zero and Het1 represents phenyl substituted in the 2- and 3-positions by a difluoromethylenedioxy group —OCF$_2$O—.

10. A compound according to claim 1, wherein R$^1$ represents phenyl substituted in the 4-position by an R$^{32}$ group, wherein R$^{32}$ is chloro, fluoro or —CF$_3$.

11. A compound according to claim 1, wherein m represents zero.

12. A compound according to claim 1, wherein m represents one and R$^3$ is located in the 5-position of the pyridyl ring.

13. A compound according to claim 12, wherein R$^3$ is methyl, chloro or fluoro.

14. The compound according to claim 1, which is:
2-(3-trifluoromethylbenzoyl)nicotinic acid (4-trifluoromethylphenyl)hydrazone;
2-(3-trifluoromethylbenzoyl)nicotinic acid (2,6-dichloro-4-trifluoromethylphenyl)hydrazone;
2-(3-trifluoromethoxybenzoyl)nicotinic acid (4-trifluoromethylphenyl)hydrazone;
2-(3-trifluoromethylbenzoyl)nicotinic acid (4-fluorophenyl)hydrazone;
2-(3-trifluoromethylbenzoyl)nicotinic acid (N-methyl-N-phenyl)hydrazone;
5-methyl-2-(3-trifluoromethoxybenzoyl)nicotinic acid (4-trifluoromethylphenyl)hydrazone;
2-(2,3-difluoromethylenedioxybenzoyl)nicotinic acid (4-fluorophenyl)hydrazone; or
N,N-dimethyl-2-(3-trifluoromethylbenzoyl)nicotinamide (4-trifluoromethylphenyl)hydrazone;
or an agriculturally acceptable salt thereof.

15. A herbicidal composition comprising:
(a) a herbicidally effective amount of compound of formula (I) as defined in claim 1, or an agriculturally acceptable salt thereof; and
(b) at least one member of the group consisting of:
(1) an agriculturally acceptable diluent or carrier; and
(2) a surface active agent.

16. A method for controlling the growth of weeds at a locus which comprises applying to the locus a herbicidally effective amount of a compound of formula (I) as defined in claim 1 or an agriculturally acceptable salt thereof.

17. A method for controlling the growth of weeds at a locus which comprises applying to the locus a herbicidally effective amount of a composition as defined in claim 15.

* * * * *